(12) United States Patent
Hirai et al.

(10) Patent No.: US 7,993,628 B2
(45) Date of Patent: Aug. 9, 2011

(54) HIGHER FATTY ACID TRIESTER AND AMIDE DERIVATIVE HAVING DIETHYLENETRIAMINE-TYPE METAL CHELATE STRUCTURE

(75) Inventors: Atsushi Hirai, Kanagawa (JP);
Kazunobu Takahashi, Kanagawa (JP);
Junji Nishigaki, Kanagawa (JP);
Kazuhiro Aikawa, Kanagawa (JP)

(73) Assignee: Fujifilm Corporation, Tokyo (JP)

(*) Notice: Subject to any disclaimer, the term of this patent is extended or adjusted under 35 U.S.C. 154(b) by 478 days.

(21) Appl. No.: 12/094,862

(22) PCT Filed: Dec. 20, 2006

(86) PCT No.: PCT/JP2006/325989
§ 371 (c)(1),
(2), (4) Date: May 23, 2008

(87) PCT Pub. No.: WO2007/072983
PCT Pub. Date: Jun. 28, 2007

(65) Prior Publication Data
US 2009/0246141 A1    Oct. 1, 2009

(30) Foreign Application Priority Data

Dec. 21, 2005 (JP) .................................. 2005-368056
Nov. 9, 2006 (JP) .................................. 2006-303863

(51) Int. Cl.
*A61K 49/04* (2006.01)
*C07C 229/26* (2006.01)

(52) U.S. Cl. .......................................... 424/9.3; 534/16
(58) Field of Classification Search .................. 424/1.21, 424/9.1, 9.3, 9.4, 450
See application file for complete search history.

(56) References Cited

U.S. PATENT DOCUMENTS 7,871,596 B2 *   1/2011   Kuniyoshi et al. ............. 424/9.1

FOREIGN PATENT DOCUMENTS

| | | |
|---|---|---|
| JP | 11-501012 A | 1/1999 |
| JP | 2000-506152 A | 5/2000 |
| JP | 2001-522348 A | 11/2001 |
| WO | 96/26180 A1 | 8/1996 |
| WO | 97/32862 A1 | 9/1997 |
| WO | 98/05626 A1 | 2/1998 |
| WO | 2006/002875 A1 | 1/2006 |

* cited by examiner

Primary Examiner — Michael G Hartley
Assistant Examiner — Jagadishwar Samala
(74) Attorney, Agent, or Firm — Sughrue Mion, PLLC

(57) ABSTRACT

A compound having superior solubility and suitable for a liposome contrast medium selective for a lesion such as vascular diseases is provided which is represented by the following general formula (I) wherein $R^1$ to $R^3$ represent an alkyl group or alkenyl group; $X^1$ and $X^2$ represent a single bond, —O—, or —N($Z^1$)- ($Z^1$ represents hydrogen atom, or an alkyl group); $X^3$ to $X^6$ represent —O—, or —N($Z^2$)- ($Z^2$ represents hydrogen atom, or an alkyl group); n represents an integer of 1 to 10; and L represents a divalent bridging group constituted by atoms selected from the group consisting of carbon atom, hydrogen atom, oxygen atom, nitrogen atom, fluorine atom and sulfur atom.

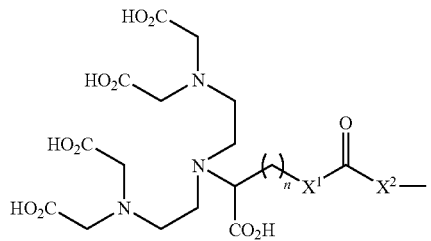

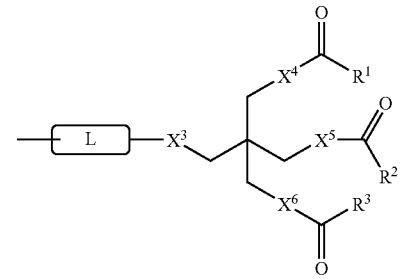

22 Claims, No Drawings

HIGHER FATTY ACID TRIESTER AND AMIDE DERIVATIVE HAVING DIETHYLENETRIAMINE-TYPE METAL CHELATE STRUCTURE

FIELD OF THE INVENTION

The present invention relates to a higher fatty acid triester and amide derivative having a diethylenetriamine-type metal chelate structure. The present invention further relates to a liposome containing the compound, a chelate compound containing the compound, or a salt of either one of said compounds as a membrane component, and a contrast medium comprising the liposome.

BACKGROUND ART

A major example of non-invasive method for diagnosing arteriosclerosis includes X-ray angiography. This method contrasts vascular flows by using a water-soluble iodine-containing contrast medium, and therefore, the method has a problem of difficulty in distinguishing pathological lesions from normal tissues. By applying the above method, only a pathological lesion where constriction progresses 50% or more can be detected, and it is difficult to detect a lesion before onset of attack of an ischemic disease.

As diagnostic methods other than the above, methods of detecting a disease by nuclear magnetic resonance tomography (MRI) using a contrast medium, which is kinetically much distributed in arteriosclerotic plaques, have been reported in recent years. However, all the compounds reported as the contrast medium have a problem for use in the diagnostic methods. For example, hematoporphyrin derivatives (see, Patent document 1) are pointed out to have a defect of, for example, dermal deposition and coloring of skin. Further, gadolinium complexes having a perfluorinated side chain (see, Non-patent document 1), reported to be accumulated in lipid-rich plaques, are concerned to be accumulated in lipid-rich tissues and organs of living bodies, such as fatty livers, renal epitheliums, and tendons of muscular tissues.

Separately reported gadolinium complexes introduced with one higher fatty acid ester group as a hydrophobic group (see, Patent document 2) have favorable solubility, and can also be used for liposome preparation. However, the complexes have a problem that the amount thereof to be incorporated into liposomes is limited to a low concentration. This is presumably because the complexes disclosed in the aforementioned publication are so-called wedge shape molecules, and therefore their compatibility with liposomes constituted by cylinder shape molecules is low.

[Patent document 1] U.S. Pat. No. 4,577,636
[Patent document 2] Japanese Patent Application No. 2005-283461
[Non-patent document 1] Circulation, 109, 2890 (2004)
[Non-patent document 2] Polymeric Materials Science and Engineering, 89, 148 (2003)
[Non-patent document 3] Inorganica Chimica Acta, 331, 151 (2002)

DISCLOSURE OF THE INVENTION

An object of the present invention is to provide a compound suitable for a liposome contrast medium for performing lesion-selective imaging, in particular, the above compound having superior solubility and superior miscibility with membrane components of liposomes. Another object of the present invention is to provide a contrast medium such as contrast medium for MRI and contrast medium for scintigraphy comprising the above compound.

The inventors of the present invention conducted various researches to achieve the aforementioned objects. As a result, they found that higher fatty acid triester and amide compounds having a diethylenetriamine-type metal chelate structure and represented by the following general formula (I) had high water-solubility and superior properties as a component of liposomes as a contrast medium. The present invention was achieved on the basis of the aforementioned finding.

The present invention thus provides a compound represented by the following general formula (I), or a salt thereof:

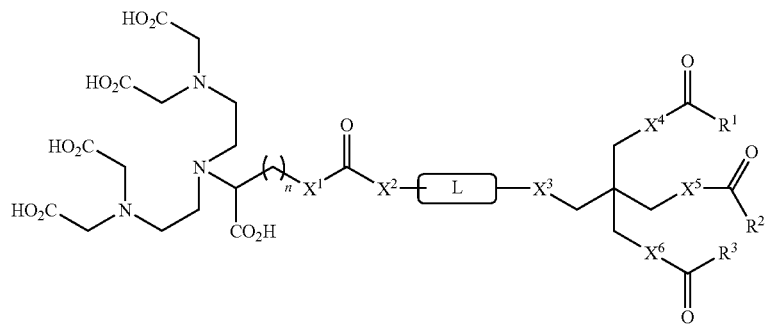

From a view point of chemical compounds, compounds having two fatty acid ester moieties are known in which phosphatidylethanolamine (PE) and diethylenetriaminepentaacetic acid (DTPA) are bound via an amide bond (for example, Non-patent document 2), and liposomes using gadolinium complexes of such compounds are also reported (Non-patent document 3). However, since these complexes are hardly soluble, they have poor property of handling in liposome formation, due to said property, they are concerned to possibly cause a problem of accumulation and toxicity in vivo.

wherein $R^1$, $R^2$ and $R^3$ independently represent an alkyl group having 8 to 30 carbon atoms, which may have a substituent, or an alkenyl group having 8 to 30 carbon atoms, which may have a substituent; $X^1$ and $X^2$ independently represent a single bond, —O—, or —N($Z^1$)- ($Z^1$ represents hydrogen atom, or an alkyl group having 1 to 3 carbon atoms), provided that $X^1$ and $X^2$ do not simultaneously represent a single bond; $X^3$, $X^4$, $X^5$ and $X^6$ independently represent —O—, or —N($Z^2$)- ($Z^2$ represents hydrogen atom, or an alkyl group having 1 to 3 carbon atoms); n represents an integer of 1 to 10; and L represents a divalent bridging group (L is constituted by atoms selected from the group consisting of carbon atom, hydrogen atom, oxygen atom, nitrogen atom, fluorine atom and sulfur atom, wherein the total number of oxygen atom constituting L is 0 to 9, that of nitrogen atom is 0 to 4, that of fluorine atom is 0 to 8, and that of sulfur atom is 0 to 2, and the total number of carbon atom, oxygen atom, nitrogen atom and sulfur atom constituting L is 1 to 20).

As preferred embodiments of the aforementioned invention, there are provided the aforementioned compound or a salt thereof, wherein $X^3$ is —O—; the aforementioned compound or a salt thereof, wherein $X^4$, $X^5$ and $X^6$ represent —O—; and the aforementioned compound or a salt thereof, wherein L is a divalent bridging group constituted by atoms selected from the group consisting of carbon atom, oxygen atom, nitrogen atom, and hydrogen atom.

As other preferred embodiments of the invention, there are provided the aforementioned compound or a salt thereof, wherein $X^2$ is —O—, or —N($Z^1$)- ($Z^1$ represents hydrogen atom, or a lower alkyl group having 1 to 3 carbon atoms), L is an alkylene group having 1 to 12 carbon atoms, or —$(CH_2CH_2Y)_mCH_2CH_2$—. -(m represents an integer of 1 to 6, Y represents —O—, or —N($Z^3$)- ($Z^3$ represents hydrogen atom, methyl group, or phenyl group), and when m is 2 or larger, two or more of groups Y may be the same or different); the aforementioned compound or a salt thereof, wherein $X^2$ is —O—, or —N($Z^1$)- ($Z^1$ represents hydrogen atom, or a lower alkyl group having 1 to 3 carbon atom); the aforementioned compound or a salt thereof, wherein L is a bridging group represented by —$(CH_2CH_2Y)_mCH_2CH_2$— (m represents an integer of 1 to 6, Y represents —O—, or —N($Z^3$)- ($Z^3$ represents hydrogen atom, methyl group, or phenyl group), and when m is 2 or larger, two or more of groups Y may be the same or different); the aforementioned compound or a salt thereof, wherein L is a bridging group represented by —$(CH_2CH_2O)_lCH_2CH_2$— (l represents an integer of 1 to 6); the aforementioned compound or a salt thereof, wherein L is a bridging group represented by -$T^1$-CO— ($T^1$ is an alkylene group having 1 to 14 carbon atoms, or a group represent by the general formula —$(CH_2CH_2Y)_u(CH_2)_h$— (u represents an integer of 1 to 6, h represents an integer of 0 to 2, Y represents —O—, or —N($Z^3$)- ($Z^3$ represents hydrogen atom, methyl group, or phenyl group), and when u is 2 or larger, two or more of groups Y may be the same or different); the aforementioned compound or a salt thereof, wherein L is a bridging group represented by -$T^2$-$X^7$CO— ($X^7$ represents —O—, or —N($Z^4$)- ($Z^4$ represents hydrogen atom, or methyl group), and $T^2$ represents an alkylene group having 1 to 14 carbon atoms); the aforementioned compound or a salt thereof, wherein L contains at least one 3- to 20-membered ring structure in the main chain thereof, and the aforementioned compound or a salt thereof, wherein $R^1$, $R^2$, and $R^3$ independently represent a linear alkyl group having 10 to 22 carbon atoms, a linear alkenyl group having 10 to 22 carbon atoms, a branched alkyl group having 10 to 22 carbon atoms, or a branched alkenyl group having 10 to 22 carbon atoms.

The present invention also provides a chelate compound, which consists of the aforementioned compound and a metal ion, or a salt thereof. As preferred embodiments of this invention, there are provided the aforementioned chelate compound or a salt thereof, wherein the metal ion is a metal ion of an element selected from those of the atomic numbers 21 to 29, 31, 32, 37 to 39, 42 to 44, 49, and 57 to 83; and the aforementioned chelate compound or a salt thereof, wherein the metal ion is a metal ion of a paramagnetic element selected from those of the atomic numbers 21 to 29, 42, 44, and 57 to 71.

From another aspect, the present invention provides a liposome containing the aforementioned compound or a salt thereof as a membrane component, and as a preferred embodiment thereof, there is provided the liposome containing a phosphatidylcholine and a phosphatidylserine as membrane components.

From a still further aspect of the present invention, there is provided a contrast medium comprising the aforementioned liposome. As preferred embodiments of this invention, there are provided the aforementioned contrast medium, which is used for imaging of a vascular disease; the aforementioned contrast medium, which is used for imaging of vascular smooth muscle cells abnormally proliferating under influence of foam macrophages; the aforementioned contrast medium, which is used for imaging of a tissue or lesion in which macrophages localize; the aforementioned contrast medium, wherein the tissue in which macrophages localize is selected from the group consisting of tissues of liver, spleen, air vesicle, lymph node, lymph vessel, and renal epithelium; and the aforementioned contrast medium, wherein the lesion in which macrophages localize is selected from the group consisting of lesions of tumor, inflammation, and infection.

From other aspects of the present invention, there are provided use of the aforementioned compound, chelate compound, or a salt of either of said compounds for the manufacture of the aforementioned contrast medium; an imaging method comprising the step of administering liposomes containing the aforementioned compound, chelate compound, or a salt of either of said compounds as a membrane component to a mammal including human, and then performing imaging; and a method for imaging a lesion of a vascular disease, which comprises the step of administering liposomes containing the aforementioned compound, chelate compound, or a salt of either of said compounds as a membrane component to a mammal including human, and then performing imaging.

BEST MODE FOR CARRYING OUT THE INVENTION $R^1$, $R^2$, and $R^3$ independently represent an alkyl group having 8 to 30 carbon atoms, or an alkenyl group having 8 to 30 carbon atoms. Although the alkyl group or alkenyl group may be any of linear, branched, and cyclic alkyl groups or alkenyl groups, and an alkyl or alkenyl group consisting a combination thereof, linear or branched groups are preferred, and both groups having no crosslinking structure are more preferred. Although $R^1$, $R^2$, and $R^3$ may be the same or different, it is preferred that these groups are the same groups. The number of the carbon atoms constituting each of $R^1$, $R^2$, and $R^3$ is more preferably 8 to 25, most preferably 10 to 22. When $R^1$, $R^2$, and $R^3$ represent an alkenyl group, the double bond thereof may be in either E- or Z-configuration, or a mixture thereof, and when the alkenyl group contains two or more double bonds, the same shall apply to each double bond. When a double bond is vicinally disubstituted, the bond is preferably in Z-configuration. Further, number and position of double bond are not particularly limited. Although the alkyl group or alkenyl group represented by $R^1$, $R^2$, and $R^3$ may have a substituent, the group may be unsubstituted. The alkyl group or alkenyl group represented by $R^1$, $R^2$, and $R^3$ is preferably unsubstituted.

In the specification, when a functional group is referred to as "substituted or unsubstituted" or "may have a substituent", it is meant that the functional group may have one or more substituents. Unless otherwise specifically mentioned, the number, substituting position, and type of substituent to be bound are not particularly limited. When a certain functional group has two or more substituents, they may be the same or different. In the specification, when a certain functional group has a substituent, examples of the substituent include a halogen atom (in the specification, the "halogen atom" may be any of fluorine, chlorine, bromine, and iodine), an alkyl group (in the specification, the "alkyl group" include straight, branched, cyclic alkyl groups, and an alkyl group consisting of a combination thereof, and the cyclic alkyl group include a polycyclic alkyl group such as a bicycloalkyl group (the same shall apply to alkyl moieties of other substituents that contain the alkyl moieties)), an alkenyl group (including a cycloalkenyl group and a bicycloalkenyl group), an alkynyl group, an aryl group, a heterocyclic group, cyano group, hydroxyl group, nitro group, carboxyl group, an alkoxyl group, an aryloxy group, a silyloxy group, a heterocyclyloxy group, an acyloxy group, carbamoyloxy group, an alkoxycarbonyloxy group, an aryloxycarbonyloxy group, amino group (including anilino group), an acylamino group, aminocarbonylamino group, an alkoxycarbonylamino group, an aryloxycarbonylamino group, sulfamoylamino group, an alkyl- or arylsulfonylamino group, mercapto group, an alkylthio group, an arylthio group, a heterocyclylthio group, sulfamoyl group, sulfo group, an alkyl- or arylsulfinyl group, an alkyl- or arylsulfonyl group, an acyl group, an aryloxycarbonyl group, an alkoxycarbonyl group, carbamoyl group, an aryl- or heterocyclylazo group, imido group, phosphino group, phosphinyl group, phosphinyloxy group, phosphinylamino group, and silyl group.

$X^1$ and $X^2$ independently represent a single bond, —O—, or —N($Z^1$)-, provided that $X^1$ and $X^2$ do not simultaneously represent a single bond. $Z^1$ represents hydrogen atom, or a lower alkyl group having 1 to 3 carbon atoms, and $Z^1$ is preferably hydrogen atom, or methyl group. $X^3$ represents —O—, or —N$Z^2$-. $Z^2$ represents hydrogen atom, or a lower alkyl group having 1 to 3 carbon atoms, and $Z^2$ is preferably hydrogen atom, or methyl group. Preferred embodiments of the groups represented by $X^1$, $X^2$, and $X^3$ are $X^1$, $X^2$, and $X^3$ at least one of which represents —O—, and most preferred are those wherein $X^3$ represents —O—.

$X^4$, $X^5$ and $X^6$ independently represent —O—, or —N($Z^2$)-. $Z^2$ represents hydrogen atom, or an alkyl group having 1 to 3 carbon atoms, and $Z^2$ is preferably hydrogen atom, or methyl group. Preferred embodiments of the groups represented by $X^4$, $X^5$, and $X^6$ are $X^4$, $X^5$, and $X^6$ at least one of which represents —O—, and most preferred are $X^4$, $X^5$, and $X^6$ all of which represent —O—.

Symbol n represents an integer of 1 to 10. Symbol n is preferably 1 to 4, most preferably 1.

L represents a divalent bridging group. L is constituted by atoms selected from the group consisting of carbon atom, hydrogen atom, oxygen atom, nitrogen atom, fluorine atom, and sulfur atom, wherein the total number of oxygen atom constituting L is 0 to 9, that of nitrogen atom is 0 to 4, that of fluorine atom is 0 to 8, and that of sulfur atom is 0 to 2, and the total number of carbon atom, oxygen atom, nitrogen atom and sulfur atom constituting L is 1 to 20. L is a divalent bridging group where the main chain (the main chain refers to an atomic group connecting $X^2$ and $X^3$ with the smallest number of atoms) is a carbon atom chain, or the main chain is constituted by an atomic chain consisting of an arbitrary combination of carbon atom and hetero atom selected from the group consisting of nitrogen atom, oxygen atom, and sulfur atom. The hetero atom is preferably nitrogen atom, or oxygen atom, and oxygen atom is most preferred. L may consist only of carbon atom and hydrogen atom.

The total number of carbon atom and hetero atom constituting L is 1 to 20, preferably 5 to 20, more preferably 8 to 18.

When L contains carbon atom and hetero atom, the total number of oxygen atom constituting L is 0 to 9, that of nitrogen atom is 0 to 4, that of fluorine atom is 0 to 8, and that of sulfur atom is 0 to 2. As for the hetero atoms constituting L, the number of oxygen atom is preferably 1 to 7, more preferably 1 to 5. The number of nitrogen atom is preferably 0 to 3, more preferably 0 to 2. The number of fluorine atom is preferably 0 to 4, and number of sulfur atom is preferably 0 or 1. The main chain of L is more preferably a chain containing oxygen atom or nitrogen atom at a ratio higher than a certain level with respect to carbon atom. When the total number of hetero atoms contained in the main chain of L, $X^2$ and $X^3$ is represented by j, and the number of carbon atoms contained in the main chain of L is represented by k, the quotient obtained by dividing k with j is preferably 3 or smaller, more preferably 2 or smaller.

In the divalent bridging group represented by L, the atoms constituting L may be contained as substituents of the aforementioned main chain. Type, number and substituting positions of the substituents are not particularly limited, and when two or more substituents exist, they may be the same or different. However, the total number of carbon atom and hetero atom constituting L including partial structures having the substituents should not exceed 20. Examples of the substituents include an alkyl group, cyano group, hydroxyl group, nitro group, carboxyl group, ether group, an acyloxy group, carbamoyloxy group, an alkoxycarbonyloxy group, amino group, an acylamino group, aminocarbonylamino group, an alkoxycarbonylamino group, sulfamoylamino group, an alkylsulfonylamino group, mercapto group, an alkylthio group, sulfamoyl group, sulfo group, an alkylsulfinyl group, an alkylsulfonyl group, an acyl group, an alkoxycarbonyl group, carbamoyl group, azo group, imido group and the like, but not limited to these. Preferred substituents are an alkyl group, oxo group, carboxyl group, hydroxyl group, ether group, an acyloxy group, carbamoyloxy group, an alkoxycarbonyloxy group, amino group, an acylamino group, an alkoxycarbonylamino group, an alkoxycarbonyl group, and carbamoyl group, and more preferred are an alkyl group, oxo group, and hydroxyl group.

Although L may be any of linear, branched and cyclic groups, and a group consisting of a combination thereof, a linear or branched group is preferred. The bridging group may be a saturated group, or a group containing an unsaturated bond. When L is a bridging group containing unsaturated bond, type, position and number of unsaturated bond are not particularly limited. Preferred example of L include an alkylene structure, a polyethylene glycol structure, a polypropylene glycol structure, a polyglycerin structure, a polyglycolic acid structure, a polylactic acid structure, a polyethyleneamine structure, a polypeptide structure, an arbitrary combination of these, and the like. More preferred are an alkylene structure, a polyethylene glycol structure, a polypropylene glycol structure, a polyethyleneamine structure, and an arbitrary combination of these, and still more preferred are an alkylene structure, a polyethylene glycol structure, a polyethyleneamine structure, and an arbitrary combination thereof. Specifically, L is preferably an alkylene group having 1 to 12 carbon atoms, or a bridging group represented by —(CH$_2$CH$_2$Y)$_m$CH$_2$CH$_2$— (m represents an integer of 1 to 6, Y represents —O—, or —N($Z^3$)- ($Z^3$ represents hydrogen atom, methyl group, or phenyl group), and when m is 2 or larger, two or more groups Y may be the same or different), more preferably a bridging group represented by —(CH$_2$CH$_2$Y)$_m$CH$_2$CH$_2$—, most preferably a bridging group represented as —(CH$_2$CH$_2$O)$_l$CH$_2$CH$_2$— (1 represents an integer of 1 to 6)-. Symbols m and l are preferably 2 to 6, more preferably 2 to 4.

In the specification, when the bridging group represented by L is represented by a chemical formula (general formula), the left end shall bind to X$^2$, and the right end shall bind to X$^3$.

Other preferred examples of L include a bridging group represented by -T$^1$-C(=O)— (T$^1$ is an alkylene group having 1 to 14 carbon atoms, or a bridging group represent by the general formula —(CH$_2$CH$_2$Y)$_u$(CH$_2$)$_h$— (u represents an integer of 1 to 6, h represents an integer of 0 to 2, Y represents —O—, or —N(Z$^3$)- (Z$^3$ represents hydrogen atom, or methyl group), and when u is 2 or larger, two or more of groups Y may be the same or different)), a bridging group represented by -T$^2$-X$^7$CO— (X$^7$ represents —O—, or —N(Z$^4$)- (Z$^4$ represents hydrogen atom, or methyl group), and T$^2$ represents an alkylene group having 1 to 14 carbon atoms), and a bridging group represented by -T$^1$-SO$_3$—.

The number of carbon atoms of the alkylene group represented by T$^1$ or T$^2$ is preferably 1 to 10, more preferably 1 to 6. Symbol u is preferably 2 to 5, more preferably 2 to 4. Symbol h is preferably 0.

Other preferred examples of L include a bridging group containing a ring structure in the main chain. The number of the members of the ring is preferably 3 to 20, more preferably 3 to 10, still more preferably 3 to 6. Although the ring structure may be constituted by atoms selected from the group consisting of carbon atom, hydrogen atom, oxygen atom, nitrogen atom, and sulfur atom, it is preferred that the ring structure is constituted by atoms selected from the group consisting of carbon atom, hydrogen atom, oxygen atom, and nitrogen atom, and it is more preferred that the ring structure is constituted by carbon atom and hydrogen atom; carbon atom, hydrogen atom and oxygen atom; or carbon atom, hydrogen atom and nitrogen atom.

Preferred examples of the ring structure include cyclopropane, cyclobutane, cyclopentane, cyclohexane, benzene, naphthalene, epoxide, oxetane, tetrahydrofuran, tetrahydropyran, crown ether, furan, pyran, aziridine, azetidine, pyrrolidine, piperidine, piperazine, imidazole, pyrrole, pyridine, tetrahydrothiophene, tetrahydrothiopyran, thiophene, thiopyran, and arbitrary combinations of these. More preferred are cyclopropane, cyclobutane, cyclopentane, cyclohexane, epoxide, oxetane, tetrahydrofuran, tetrahydropyran, crown ether, aziridine, azetidine, pyrrolidine, piperidine, piperazine and arbitrary combinations of these, and still more preferred are cyclopropane, cyclopentane, cyclohexane, epoxide, tetrahydrofuran, tetrahydropyran, crown ether, aziridine, pyrrolidine, piperidine, piperazine, and arbitrary combinations thereof. Moreover, the ring structure may consist of two or more (preferably 2 to 4, more preferably 2) rings, such as a condensed ring structure, a crosslinked structure, and a spiro structure. The ring contained in the main chain of L is most preferably a monocyclic ring.

Preferred examples of the compound of the present invention will be mentioned below. However, the compound of the present invention is not limited to these examples. In the following tables, Me represents methyl group, Et represents ethyl group, and Pr represents propyl group.

TABLE 1

| No. | n | X$^1$ | X$^2$ | L | X$^3$ | X$^4$ | X$^5$ | X$^6$ | R$^1$, R$^2$, R$^3$ |
|---|---|---|---|---|---|---|---|---|---|
| 1 | 1 | — | O | ((CH$_2$)$_2$O)$_3$(CH$_2$)$_2$ | NH | O | O | O | n-C$_{15}$H$_{31}$ |
| 2 | 1 | — | O | ((CH$_2$)$_2$O)$_3$(CH$_2$)$_2$ | NMe | NH | NH | NH | n-C$_{15}$H$_{31}$ |
| 3 | 2 | — | NH | ((CH$_2$)$_2$O)$_3$(CH$_2$)$_2$ | O | O | NEt | NEt | n-C$_{15}$H$_{31}$ |
| 4 | 2 | — | NMe | ((CH$_2$)$_2$O)$_3$(CH$_2$)$_2$ | O | O | O | O | n-C$_{15}$H$_{31}$ |
| 5 | 2 | — | NH | ((CH$_2$)$_2$O)$_3$(CH$_2$)$_2$ | NH | O | O | O | n-C$_{15}$H$_{31}$ |
| 6 | 3 | O | NH | ((CH$_2$)$_2$O)$_3$(CH$_2$)$_2$ | NH | O | O | O | n-C$_{15}$H$_{31}$ |
| 7 | 3 | O | O | ((CH$_2$)$_2$O)$_3$(CH$_2$)$_2$ | NEt | O | O | O | n-C$_{15}$H$_{31}$ |
| 8 | 4 | NH | — | ((CH$_2$)$_2$O)$_3$(CH$_2$)$_2$ | O | O | O | O | n-C$_{15}$H$_{31}$ |
| 9 | 4 | NH | NH | ((CH$_2$)$_2$O)$_3$(CH$_2$)$_2$ | O | O | O | O | n-C$_{15}$H$_{31}$ |
| 10 | 4 | NMe | NMe | (CH$_2$)$_2$O(CH$_2$)$_5$O(CH$_2$)$_2$ | NH | NH | NMe | NEt | n-C$_{15}$H$_{31}$ |
| 11 | 5 | — | O | (CH$_2$)$_3$SO$_2$NH(CH$_2$)$_3$ | O | O | O | O | n-C$_8$H$_{17}$ |
| 12 | 5 | — | O | (CH$_2$)$_3$S(CH$_2$)$_3$ | O | O | O | O | n-C$_{10}$H$_{21}$ |
| 13 | 6 | — | O | (CH$_2$)$_3$N(C$_6$H$_5$)(CH$_2$)$_3$ | O | O | O | O | n-C$_{13}$H$_{29}$ |
| 14 | 6 | — | O | (CH$_2$)$_3$S(=O)(CH$_2$)$_3$ | O | O | O | O | n-C$_{15}$H$_{31}$ |
| 15 | 8 | — | O | (CH$_2$)$_3$S(CH$_2$)$_3$ | O | O | NH | NH | n-C$_{17}$H$_{35}$ |
| 16 | 8 | — | O | (CH$_2$)$_3$S(=O)(CH$_2$)$_3$S(=O)(CH$_2$)$_3$ | O | O | O | O | n-C$_{20}$H$_{41}$ |
| 17 | 10 | — | NPr | (CH$_2$)$_3$S(CH$_2$)$_3$ | O | O | O | O | n-C$_{25}$H$_{51}$ |
| 18 | 10 | — | O | (CH$_2$)$_3$S(=O)$_2$(CH$_2$)$_3$ | O | O | O | O | n-C$_{30}$H$_{61}$ |
| 19 | 1 | — | O | ((CH$_2$)$_2$O)$_3$(CH$_2$)$_2$ | O | O | O | O | (Z)-(CH$_2$)$_7$CH=CH(CH$_2$)$_7$CH$_3$ |
| 20 | 1 | — | O | ((CH$_2$)$_2$O)$_3$(CH$_2$)$_2$ | O | O | O | O | (Z,Z)-(CH$_2$)$_7$(CH=CHCH$_2$)$_2$(CH$_2$)$_3$CH$_3$ |
| 21 | 1 | — | O | ((CH$_2$)$_2$O)$_3$(CH$_2$)$_2$ | O | O | O | NH | (Z,Z,Z)-(CH$_2$)$_7$(CH=CHCH$_2$)$_3$CH$_3$ |
| 22 | 1 | — | O | ((CH$_2$)$_2$O)$_3$(CH$_2$)$_2$ | O | O | O | O | CH$_2$CH(CH$_3$)(CH$_2$)$_3$CH(CH$_3$)$_2$ |
| 23 | 1 | — | O | ((CH$_2$)$_2$O)$_3$(CH$_2$)$_2$ | O | O | O | O | CH$_2$(CH(CH$_3$)(CH$_2$)$_3$)$_2$CH(CH$_3$)$_2$ |

TABLE 1-continued

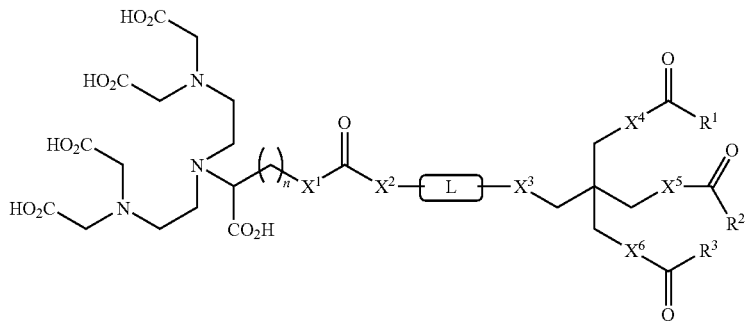

| No. | n | X¹ | X² | L | X³ | X⁴ | X⁵ | X⁶ | R¹, R², R³ |
|---|---|---|---|---|---|---|---|---|---|
| 24 | 1 | — | O | $((CH_2)_2O)_3(CH_2)_2$ | O | O | NH | NH | $CH_2(CH(CH_3)(CH_2)_3)_3CH(CH_3)_2$ |
| 25 | 1 | — | O | $((CH_2)_2O)_3(CH_2)_2$ | O | O | O | O | $(E)-CH_2CH=C(CH_3)(CH_2)_2CH=C(CH_3)_2$ |
| 26 | 1 | — | O | $((CH_2)_2O)_3(CH_2)_2$ | O | O | O | O | $(Z)-CH_2CH=C(CH_3)(CH_2)_2CH=C(CH_3)_2$ |
| 27 | 1 | — | O | $((CH_2)_2O)_3(CH_2)_2$ | O | O | O | O | $(E,E)-(CH_2CH=C(CH_3)(CH_2))_2CH_2CH=C(CH_3)_2$ |
| 28 | 1 | — | O | $((CH_2)_2O)_3(CH_2)_2$ | O | O | O | O | $CH_2(CHCH_3(CH_2)_2CH=C(CH_3))_2$ |
| 29 | 1 | — | O | $((CH_2)_2O)_3(CH_2)_2$ | O | O | O | O | $CH_2CH(C_6H_{13})C_8H_{17}$ |
| 30 | 1 | — | O | $((CH_2)_2O)_3(CH_2)_2$ | O | O | O | O | $(C(CH_3)_2CH_2)_2C(CH_3)_3$ |
| 31 | 1 | — | O | $((CH_2)_2O)_3(CH_2)_2$ | O | O | O | O | $n-C_{15}H_{31}$ |
| 32 | 1 | — | O | $(CH_2)_8CO$ | O | O | O | O | $(Z)-(CH_2)_7CH=CH(CH_2)_7CH_3$ |

In the table, — represents a single bond. Me represents methyl group, Et represents ethyl group, and Pr represents a propyl group.

In the table, — represents a single bond, Me represents methyl group, Pr represents a propyl group, and t-Bu represents tertiary butyl group.

TABLE 2

| No. | n | X¹ | X² | L | X³ | X⁴, X⁵, X⁶ | R¹, R², R³ |
|---|---|---|---|---|---|---|---|
| 101 | 1 | — | O | $(CH_2)_2O(CH_2)_2$ | O | O | $n-C_{15}H_{31}$ |
| 102 | 1 | — | O | $((CH_2)_2O)_2(CH_2)_2$ | O | O | $n-C_{15}H_{31}$ |
| 103 | 1 | — | O | $((CH_2)_2O)_3(CH_2)_2$ | O | O | $n-C_{15}H_{31}$ |
| 104 | 1 | — | O | $((CH_2)_2O)_4(CH_2)_2$ | O | O | $n-C_{15}H_{31}$ |
| 105 | 1 | — | O | $((CH_2)_2O)_5(CH_2)_2$ | O | O | $n-C_{15}H_{31}$ |
| 106 | 1 | — | O | $(CH_2)_2OCO_2(CH_2)_2$ | O | O | $n-C_{15}H_{31}$ |
| 107 | 1 | — | O | $(CH_2)_2NHCONH(CH_2)_2$ | O | O | $n-C_{15}H_{31}$ |
| 108 | 1 | — | O | $(CH_2)_2NH(CH_2)_2N(COCH_3)(CH_2)_2$ | O | O | $n-C_{15}H_{31}$ |
| 109 | 1 | — | O | $(CH_2)_2NMe(CH_2)_2$ | O | O | $n-C_{15}H_{31}$ |
| 110 | 1 | — | O | $(CH_2)_4N(CO_2t-Bu)(CH_2)_4$ | O | O | $n-C_{15}H_{31}$ |
| 111 | 1 | — | NH | $((CH_2)_2NH)_4(CH_2)_2$ | NPr | O | $n-C_{15}H_{31}$ |
| 112 | 1 | — | O | $((CH_2)_3O)_3(CH_2)_3$ | O | O | $n-C_{15}H_{31}$ |
| 113 | 1 | — | NH | $((CH_2)_2NMe)_4(CH_2)_2$ | NH | O | $n-C_{15}H_{31}$ |
| 114 | 1 | — | O | $((CH_2)_2OCH_2CH(CN)CH_2O(CH_2)_2$ | O | O | $n-C_{15}H_{31}$ |
| 115 | 1 | — | O | $(CH_2)_2OCH_2CH(OH)CH_2O(CH_2)_2$ | O | O | $n-C_{15}H_{31}$ |
| 116 | 1 | — | O | $(CH_2)_2OCH_2CH(OH)(CH_2)_4CH(OH)CH_2O(CH_2)_2$ | O | O | $n-C_{15}H_{31}$ |
| 117 | 1 | — | O | $CH_2(CH(OH)CH_2OCH_2)_3CH(OH)CH_2$ | O | O | $n-C_{15}H_{31}$ |
| 118 | 1 | — | O | $(CH_2)_2O(CH_2)_2NC_6H_5(CH_2)_2O(CH_2)_2$ | O | O | $n-C_{15}H_{31}$ |
| 119 | 1 | — | O | $(CH_2)_2O(CH_2)_2NOH(CH_2)_2O(CH_2)_2$ | O | O | $n-C_{15}H_{31}$ |
| 120 | 1 | — | O | $(CH_2)_2C(=O)OCH_2(CH(OH))_4CH_2OC(=O)(CH_2)_2$ | O | O | $n-C_{15}H_{31}$ |
| 121 | 1 | — | O | $(CH_2)_2N(CH_2CONH_2)(CH_2)_2N(CH_2CONH_2)(CH_2)_2$ | O | O | $n-C_{15}H_{31}$ |
| 122 | 1 | — | O | $CH_2C(CONH_2)NHCOCH(CH_2OH)NHCOCH(CH_2OH)$ | NH | O | $n-C_{15}H_{31}$ |
| 123 | 1 | — | O | $((CH_2)_2O)_2(CHCONH_2)_2(O(CH_2)_2)_2$ | O | O | $n-C_{15}H_{31}$ |
| 124 | 1 | — | O | $((CH_2)_2O)_2(CHCONHOH)_2(O(CH_2)_2)_2$ | O | O | $n-C_{15}H_{31}$ |
| 125 | 1 | O | — | $(CH_2)_2OC(=O)(CH_2)_2OC(=O)(CH_2)_2$ | O | O | $n-C_{15}H_{31}$ |
| 126 | 1 | O | — | $CH(CH_3)O(C(=O)CH(CH_3)O)_2C(=O)CH(CH_3)$ | O | O | $n-C_{15}H_{31}$ |
| 127 | 1 | O | — | $CH_2$ | O | O | $n-C_{15}H_{31}$ |
| 128 | 1 | — | O | $(CH_2)_7$ | O | O | $n-C_{15}H_{31}$ |
| 129 | 1 | — | O | $(CH_2)_{12}$ | O | O | $n-C_{15}H_{31}$ |
| 130 | 1 | — | O | $(CH_2)_2(CF_2)_4(CH_2)_2$ | O | O | $n-C_{15}H_{31}$ |
| 131 | 1 | — | O | $CH_2CHFCH_2$ | O | O | $n-C_{15}H_{31}$ |
| 132 | 1 | O | — | $(CH(OH))_9CH_2$ | O | O | $n-C_{15}H_{31}$ |
| 133 | 1 | — | O | $(CH_2CH(CH_2OH)O)_2CH_2CH(CHOH)$ | O | O | $n-C_{15}H_{31}$ |

TABLE 3

| No. | n | $X^1$ | $X^2$ | L | $X^3$ | $X^4$ | $X^5$ | $X^6$ | $R^1$ |
|---|---|---|---|---|---|---|---|---|---|
| 201 | 1 | — | O | $(CH_2)_7$ | O | O | NH | NH | $n\text{-}C_{15}H_{31}$ |
| 202 | 1 | — | O | $(CH_2)_7$ | O | O | O | O | $n\text{-}C_{15}H_{31}$ |
| 203 | 1 | — | O | $(CH_2)_7$ | O | O | O | O | $n\text{-}C_{15}H_{31}$ |
| 204 | 1 | — | O | $(CH_2)_7(C=O)$ | O | O | O | O | $n\text{-}C_{15}H_{31}$ |
| 205 | 1 | — | O | $(CH_2)_7(C=O)$ | NH | O | O | O | $n\text{-}C_{15}H_{31}$ |
| 206 | 1 | — | O | $((CH_2)_2O)_3(CH_2)_2$ | O | O | O | O | $n\text{-}C_{15}H_{31}$ |
| 207 | 1 | — | O | $(CH_2)_7$ | O | O | O | O | $n\text{-}C_{15}H_{31}$ |
| 208 | 1 | — | O | $(CH_2)_7$ | O | O | O | O | $n\text{-}C_{15}H_{31}$ |
| 209 | 1 | — | O | $(CH_2)_8CO$ | O | O | O | O | $n\text{-}C_{15}H_{31}$ |

| No. | $R^2$ | $R^3$ |
|---|---|---|
| 201 | $n\text{-}C_{15}H_{31}$ | $n\text{-}C_{17}H_{35}$ |
| 202 | $n\text{-}C_{17}H_{35}$ | $n\text{-}C_{19}H_{39}$ |
| 203 | $(Z)\text{-}(CH_2)_7CH=CH(CH_2)_7CH_3$ | $(Z,Z)\text{-}(CH_2)_7(CH=CHCH_2)_2(CH_2)_3CH_3$ |
| 204 | $CH_2(CH(CH_3)(CH_2)_3)_3CH(CH_3)_2$ | $CH_2(CH(CH_3)(CH_2)_3)_3CH(CH_3)_2$ |
| 205 | $(C(CH_3)_2CH_2)_2C(CH_3)_3$ | $CH_2CH(CH_3)(CH_2)_3CH(CH_3)_2$ |
| 206 | $CH_2(CH(CH_3)(CH_2)_3)_3CH(CH_3)_2$ | $CH_2(CH(CH_3)(CH_2)_3)_3CH(CH_3)_2$ |
| 207 | $CH_2CHCH_3(CH_2)_2CH=C(CH_3)_2$ | $CH_2CHCH_3(CH_2)_2CH=C(CH_3)_2$ |
| 208 | $CH_2CH(C_6H_{13})C_8H_{17}$ | $CH_2CH(C_6H_{13})C_8H_{17}$ |
| 209 | $(Z)\text{-}(CH_2)_7CH=CH(CH_2)_7CH_3$ | $(Z)\text{-}(CH_2)_7CH=CH(CH_2)_7CH_3$ |

In the table, — represents a single bond

TABLE 4

| No. | n | $X^1$ | $X^2$ | L | $X^3$ | $X^4, X^5, X^6$ | $R^1, R^2, R^3$ |
|---|---|---|---|---|---|---|---|
| 301 | 1 | — | O | $CH_2C(=O)$ | O | O | $n\text{-}C_{15}H_{31}$ |
| 302 | 1 | — | O | $(CH_2)_5C(=O)$ | O | O | $n\text{-}C_{15}H_{31}$ |
| 303 | 1 | — | O | $(CH_2)_8C(=O)$ | O | O | $n\text{-}C_{15}H_{31}$ |
| 304 | 1 | — | O | $(CH_2)_{11}C(=O)$ | O | O | $n\text{-}C_{15}H_{31}$ |
| 305 | 1 | — | O | $(CH_2)_{14}C(=O)$ | O | O | $n\text{-}C_{15}H_{31}$ |
| 306 | 1 | — | O | $((CH_2)_2O)_2CH_2C(=O)$ | O | O | $n\text{-}C_{15}H_{31}$ |
| 307 | 1 | — | O | $((CH_2)_2O)_2(CH_2)_2C(=O)$ | O | O | $n\text{-}C_{15}H_{31}$ |
| 308 | 1 | — | O | $((CH_2)_2O)_3CH_2C(=O)$ | O | O | $n\text{-}C_{15}H_{31}$ |
| 309 | 1 | — | O | $((CH_2)_2O)_4CH_2C(=O)$ | O | O | $n\text{-}C_{15}H_{31}$ |
| 310 | 1 | — | O | $((CH_2)_2O)_5CH_2C(=O)$ | O | O | $n\text{-}C_{15}H_{31}$ |
| 311 | 1 | — | O | $((CH_2)_2O)_5(CH_2)_2C(=O)$ | O | O | $n\text{-}C_{15}H_{31}$ |
| 312 | 1 | — | NH | $((CH_2)_2O)_2(CH_2)_2NH(CH_2)_2C(=O)$ | O | O | $n\text{-}C_{15}H_{31}$ |
| 313 | 1 | — | O | $(CH_2)_6S(=O)_2$ | NH | O | $n\text{-}C_{15}H_{31}$ |

TABLE 5

| No. | n | $X^1$ | $X^2$ | L | $X^3$ | $X^4, X^5, X^6$ | $R^1, R^2, R^3$ |
|---|---|---|---|---|---|---|---|
| 401 | 1 | — | O | $(CH_2)_2OC(=O)$ | O | O | $n\text{-}C_{15}H_{31}$ |
| 402 | 1 | — | O | $(CH_2)_4OC(=O)$ | O | O | $n\text{-}C_{15}H_{31}$ |
| 403 | 1 | — | O | $(CH_2)_8OC(=O)$ | O | O | $n\text{-}C_{15}H_{31}$ |
| 404 | 1 | — | O | $(CH_2)_{14}OC(=O)$ | O | O | $n\text{-}C_{15}H_{31}$ |
| 405 | 1 | — | O | $(CH_2)_{17}OC(=O)$ | O | O | $n\text{-}C_{15}H_{31}$ |
| 406 | 1 | — | O | $((CH_2)_2O)_2C(=O)$ | O | O | $n\text{-}C_{15}H_{31}$ |
| 407 | 1 | — | O | $((CH_2)_2O)_3C(=O)$ | O | O | $n\text{-}C_{15}H_{31}$ |
| 408 | 1 | — | O | $((CH_2)_2O)_4C(=O)$ | O | O | $n\text{-}C_{15}H_{31}$ |
| 409 | 1 | — | O | $((CH_2)_2O)_5C(=O)$ | O | O | $n\text{-}C_{15}H_{31}$ |
| 410 | 1 | — | O | $((CH_2)_2O)_6C(=O)$ | O | O | $n\text{-}C_{15}H_{31}$ |
| 411 | 1 | — | NH | $((CH_2)_2NH)_2C(=O)$ | O | O | $n\text{-}C_{15}H_{31}$ |
| 412 | 1 | — | NH | $((CH_2)_2O(CH_2)_2NH)_3C(=O)$ | O | O | $n\text{-}C_{15}H_{31}$ |
| 413 | 1 | — | NH | $((CH_2)_2NH)_2C(=O)$ | NH | O | $n\text{-}C_{15}H_{31}$ |
| 414 | 1 | — | NH | $(CH_2)_2NC_6H_5(CH_2)_2OC(=O)$ | NH | O | $n\text{-}C_{15}H_{31}$ |
| 415 | 1 | — | NH | $((CH_2)_2O(CH_2)_2NH)_3C(=O)$ | O | O | $n\text{-}C_{15}H_{31}$ |

TABLE 6
| No. | n | X¹ | X² | L | X³ | X⁴ | X⁵ | X⁶ | R¹, R², R³ |
|---|---|---|---|---|---|---|---|---|---|
| 501 | 1 | — | O |  | NH | O | O | O | n-C$_{15}$H$_{31}$ |
| 502 | 1 | — | O | 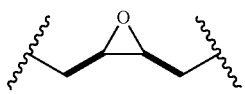 | NMe | NH | NH | NH | n-C$_{15}$H$_{31}$ |
| 503 | 2 | — | NH | 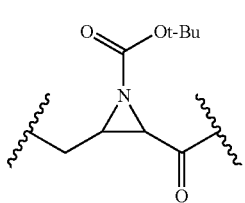 | O | O | NEt | NEt | n-C$_{15}$H$_{31}$ |
| 504 | 2 | — | NMe | 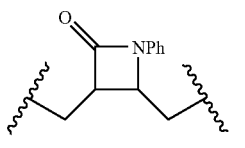 | O | O | O | O | n-C$_{15}$H$_{31}$ |
| 505 | 2 | — | NH | 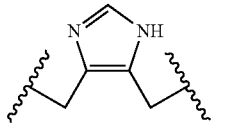 | NH | O | O | O | n-C$_{15}$H$_{31}$ |
| 506 | 3 | O | NH | 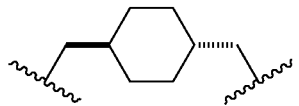 | NH | O | O | O | n-C$_{15}$H$_{31}$ |
| 507 | 3 | O | O | 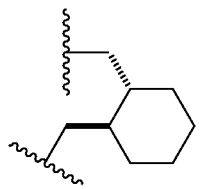 | NEt | O | O | O | n-C$_{15}$H$_{31}$ |
| 508 | 4 | NH | — | 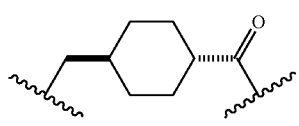 | O | O | O | O | n-C$_{15}$H$_{31}$ |
| 509 | 4 | NH | NH | 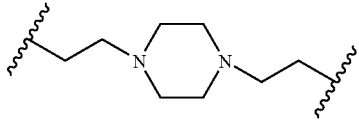 | NH | O | O | O | n-C$_{15}$H$_{31}$ |
| 510 | 4 | NMe | NMe | 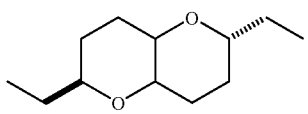 | NH | NH | NMe | NEt | n-C$_{15}$H$_{31}$ |
| 511 | 5 | — | O | 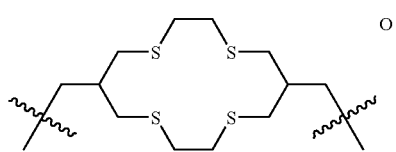 | O | O | O | O | n-C$_8$H$_{17}$ |

TABLE 6-continued
| No. | n | X¹ | X² | L | X³ | X⁴ | X⁵ | X⁶ | R¹, R², R³ |
|---|---|---|---|---|---|---|---|---|---|
| 512 | 5 | — | O | 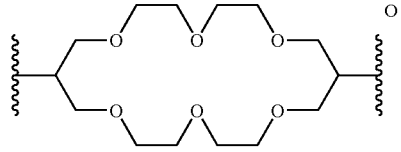 | O | O | O | O | n-$C_{10}H_{21}$ |
| 513 | 6 | — | O | 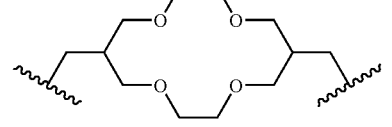 | O | O | O | O | n-$C_{13}H_{29}$ |
| 514 | 6 | — | O | 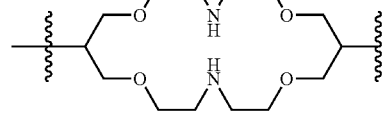 | O | O | O | O | n-$C_{15}H_{31}$ |
| 515 | 8 | — | O | 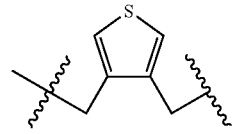 | O | O | NH | NH | n-$C_{17}H_{35}$ |
| 516 | 8 | — | O | 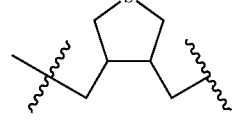 | O | O | O | O | n-$C_{20}H_{41}$ |
| 517 | 10 | — | NPr | 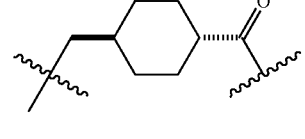 | O | O | O | O | n-$C_{25}H_{51}$ |
| 518 | 10 | — | O | 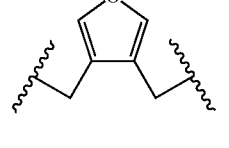 | O | O | O | O | n-$C_{30}H_{61}$ |
| 519 | 1 | — | O | 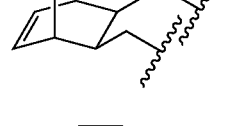 | O | O | O | O | (Z)-$(CH_2)_7CH=CH(CH_2)_7CH_3$ |
| 520 | 1 | — | O | 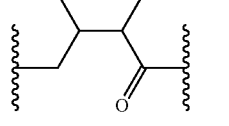 | O | O | O | O | (Z,Z)-$(CH_2)_7(CH=CHCH_2)_2(CH_2)_3CH_3$ |
| 521 | 1 | — | O | 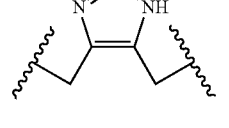 | O | O | O | NH | (Z,Z,Z)-$(CH_2)_7(CH=CHCH_2)_3CH_3$ |

TABLE 6-continued

| No. | n | X¹ | X² | L | X³ | X⁴ | X⁵ | X⁶ | R¹, R², R³ |
|---|---|---|---|---|---|---|---|---|---|
| 522 | 1 | — | O | (5-indolyl, N-linked) | O | O | O | O | $CH_2CH(CH_3)(CH_2)_3CH(CH_3)_2$ |
| 523 | 1 | — | O | (5-indolyl-2-carbonyl) | O | O | O | O | $CH_2(CH(CH_3)(CH_2)_3)_2CH(CH_3)_2$ |
| 524 | 1 | — | O | (steroid with OH) | O | O | NH | NH | $CH_2(CH(CH_3)(CH_2)_3)_3CH(CH_3)_2$ |
| 525 | 1 | — | O | (bicyclohexyl with ketone) | O | O | O | O | (E)-$CH_2CH=C(CH_3)(CH_2)_2CH=C(CH_3)_2$ |
| 526 | 1 | — | O | (1,5-naphthyl) | O | O | O | O | (Z)-$CH_2CH=C(CH_3)(CH_2)_2CH=C(CH_3)_2$ |
| 527 | 1 | — | O | (1,2-cyclohexyl) | O | O | O | O | (E,E)-$(CH_2(CH=C(CH_3)(CH_2))_2CH_2CH=C(CH_3)_2$ |
| 528 | 1 | — | NH | (1,2-cyclohexyl) | NH | O | O | O | $CH_2(CHCH_3(CH_2)_2CH=C(CH_3)_2$ |
| 529 | 1 | — | O | (1,4-phenyl with ketone) | O | O | O | O | $CH_2CH(C_6H_{13})C_8H_{17}$ |

TABLE 6-continued

| No. | n | $X^1$ | $X^2$ | L | $X^3$ | $X^4$ | $X^5$ | $X^6$ | $R^1, R^2, R^3$ |
|---|---|---|---|---|---|---|---|---|---|
| 530 | 1 | — | O | ![structure] | O | O | O | O | $(C(CH_3)_2CH_2)_2C(CH_3)_3$ |
| 531 | 1 | — | O | ![structure] | O | O | O | O | $n-C_{15}H_{31}$ |

In the table, —represents a single bond Me represents methyl group, Et represents ethyl group, and Pr represents a propyl group.

TABLE 7

| No. | n | $X^1$ | $X^2$ | L | $X^3$ | $X^4$ | $X^5$ | $X^6$ | $R^1$ | $R^2$ | $R^3$ |
|---|---|---|---|---|---|---|---|---|---|---|---|
| 601 | 1 | — | O | cyclohexane | O | O | NH | NH | n-$C_{15}H_{31}$ | n-$C_{15}H_{31}$ | n-$C_{17}H_{35}$ |
| 602 | 1 | — | O | cyclohexane | O | O | O | O | n-$C_{15}H_{31}$ | n-$C_{17}H_{35}$ | n-$C_{19}H_{39}$ |
| 603 | 1 | — | O | cyclohexane | O | O | O | O | n-$C_{15}H_{31}$ | (Z)-($CH_2$)$_7$CH=CH($CH_2$)$_7$$CH_3$ | (Z,Z)-($CH_2$)$_7$(CH=CH$CH_2$)$_2$($CH_2$)$_3$$CH_3$ |
| 604 | 1 | — | O | cyclohexane | O | O | O | O | n-$C_{15}H_{31}$ | $CH_2$(CH($CH_3$)($CH_2$)$_3$)$_3$CH($CH_3$)$_2$ | $CH_2$(CH($CH_3$)($CH_2$)$_3$)$_3$CH($CH_3$)$_2$ |
| 605 | 1 | — | O | cyclohexane | O | O | O | O | n-$C_{15}H_{31}$ | (C($CH_3$)$_2$$CH_2$)$_2$C($CH_3$)$_3$ | $CH_2$CH($CH_3$)($CH_2$)$_3$CH($CH_3$)$_2$ |

TABLE 7-continued
| No. | n | $X^1$ | $X^2$ | L | $X^3$ | $X^4$ | $X^5$ | $X^6$ | $R^1$ | $R^2$ | $R^3$ |
|---|---|---|---|---|---|---|---|---|---|---|---|
| 606 | 1 | — | O | 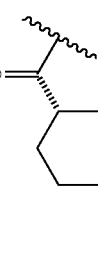 | O | O | O | O | n-$C_{15}H_{31}$ | $CH_2(CH(CH_3)(CH_2)_3)_3CH(CH_3)_2$ | $CH_2(CH(CH_3)(CH_2)_3)_3CH(CH_3)_2$ |
| 607 | 1 | — | O |  | O | O | O | O | n-$C_{15}H_{31}$ | $CH_2(CHCH_3(CH_2)_2)_2CH=C(CH_3)_2$ | $CH_2(CHCH_3(CH_2)_2)_2CH=C(CH_3)_2$ |
| 608 | 1 | — | O | 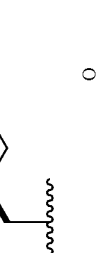 | O | O | O | O | n-$C_{15}H_{31}$ | $CH_2CH(C_6H_{13})C_6H_{17}$ | $CH_2CH(C_6H_{13})C_8H_{17}$ |

In the table, —represents a single bond

Synthetic methods for the compound of the present invention, in general, will be explained. However, synthetic methods of the compound of the present invention are not limited to these methods. As the long chain fatty acids as a partial structure of the compound of the present invention, those ordinarily commercially available may be used, or they may be suitably synthesized depending on purposes. When they are obtained by syntheses, corresponding alcohols, alkyl halides and the like can be used as raw materials according to, for example, the method described by Richard C. Larock in Comprehensive Organic Transformations (VCH).

The aforementioned long chain fatty acids can be condensed with a pentaerythritol derivative to form a triacyl compound, then coupled with an α,ω-diol or diamine, such as diethylene glycol, diethanolamine, and diethylenetriamine, an α-amino-ω-alcohol, ω-hydroxycarboxylic acid, ω-hydroxysulfonic acid, 1-imidazolidylformic acid ω-hydroxy ester, ω-aminocarboxylic acid, or the like, and thereby derived into a triacyl-ω-alcohol or amine. In this process, a protective group can also be used, if necessary. As a protective group used in such process, for example, any of the protective groups described by T. W. Green & P. G. M. Wuts in Protecting Groups in Organic Synthesis (John Wiley & Sonc, Inc.) can be suitably selected and used.

The aforementioned triacyl-ω-alcohol or amine compound can be bound with a polyamine derivative having a metal coordinating ability to synthesize the compound of the present invention. As for the method for preparation, the compound can be synthesized according to, for example, the method described in Bioconjugate Chem., 10, 137 (1999). However, this method is a mere example, and the method is not limited to the above method.

The chelate compound of the present invention consists of the aforementioned compound and a metal ion. Although type of the metal ion is not particularly limited, metal ions of paramagnetic metals, heavy metals, and radioactive metals of radioactive metal isotopes are preferably used as metal ions suitable for the purpose of imaging by MRI, X-ray, ultrasonic contrast, positron emission tomography (PET), scintigraphy, and the like, or radiotherapy. More specifically, metal ions of elements selected from those of the atomic numbers 21 to 29, 31, 32, 37 to 39, 42 to 44, 49, and 57 to 83 are preferred. Examples of metal ions suitable for use of the chelate compound of the present invention as a contrast medium for MRI include metal ions of elements of the atomic numbers 21 to 29, 42, 44 and 57 to 71. For use in the preparation of positive MRI contrast medium, more preferred metals are those of the atomic numbers 24 (Cr), 25 (Mn), 26 (Fe), 63 (Eu), 64 (Gd), 66 (Dy), and 67 (Ho). For use in the preparation of negative MRI contrast medium, more preferred metals are those of the atomic numbers 62 (Sm), 65 (Tb), and 66 (Dy). Most preferred are those of the atomic numbers 25 (Mn), 26 (Fe), and 64 (Gd), and Mn(II), Fe(III), and Gd(III) are especially preferred.

The compound and chelate compound of the present invention may have one or more asymmetric centers. In such compounds, stereoisomers such as optically active substances and diastereomers based on the asymmetric centers may exist. Any of arbitrary stereoisomers in pure forms, arbitrary mixtures of stereoisomers, racemates and the like fall within the scope of the present invention. Further, the compound of the present invention may have one or more olefinic double bonds. The configuration thereof may be either E-configuration or Z-configuration, or the compound may be present as a mixture thereof. The compound of the present invention may also exist as tautomers. Any tautomers or mixtures thereof fall within the scope of the present invention. Further, the compound of the present invention may form a salt, and the compound in a free form and the compound in the form of a salt may form a hydrate or a solvate. All of these substances also fall within the scope of the present invention. Type of the salt is not particularly limited, and the salt may be an acid addition salt, or a base addition salt.

The compound or chelate compound of the present invention having one or more nuclear species emitting positrons may be used for imaging by PET. More specifically, besides the aforementioned chelate compound, a compound obtained by incorporating a nuclear species emitting positrons into the compound of the present invention can be preferably used as a medium for the imaging. Preferred examples of the nuclear species used for the purpose of the incorporation into the compound include $^{11}C$, $^{13}N$, $^{15}O$, and $^{18}F$. More preferred nuclear species are $^{11}C$ and $^{18}F$.

The compound of the present invention and a salt thereof can be used as a membrane component of a liposome. When a liposome is prepared by using the compound of the present invention or a salt thereof, amount of the compound of the present invention or a salt thereof is about from 10 to 90 mass %, preferably from 10 to 80 mass %, more preferably from 20 to 80 mass %, based on the total mass of membrane components. Although one kind of the compound of the present invention may be used as the membrane component, two or more kinds of the compounds may be used in combination.

As other membrane components of liposome, any of lipid compounds ordinarily used for the preparation of liposomes can be used. Such compounds are described in, for example, Biochim. Biophys. Acta, 150 (4), 44 (1982); Adv. in Lipid. Res., 16 (1) 1 (1978); RESEARCH IN LIPOSOMES, P. Machy, L. Leserman, John Libbey EUROTEXT Co.; "Liposome", Ed., Nojima, Sunamoto and Inoue, Nankodo, and the like. As the lipid compounds, phospholipids are preferred, and phosphatidylcholines (PC) are particularly preferred. Preferred examples of phosphatidylcholines include egg PC (PC derived from egg), dimyristoyl-PC (DMPC), dipalmitoyl-PC (DPPC), distearoyl-PC (DSPC), dioleyl-PC (DOPC), and the like. However, PCs are not limited to these examples.

Preferred examples of the membrane components of liposomes include a combination of a phosphatidylcholine and a phosphatidylserine (PS). Examples of the phosphatidylserine include those having lipid moieties similar to those of the phospholipids mentioned as preferred examples of the phosphatidylcholines. When a phosphatidylcholine and a phosphatidylserine are used in combination, molar ratio of PC and PS (PC:PS) used is preferably in the range of 90:10 to 10:90, more preferably 30:70 to 70:30.

Another preferred embodiment of the liposome of the present invention includes a liposome containing a phosphatidylcholine and a phosphatidylserine and further containing a phosphoric acid dialkyl ester as membrane components. The two alkyl groups constituting the dialkyl ester of phosphoric acid dialkyl ester are preferably the same, and each alkyl group preferably contains 6 or more carbon atoms, more preferably 10 or more carbon atoms, still more preferably 12 or more carbon atoms. Preferred examples of the phosphoric acid dialkyl ester include, but not limited to, dilauryl phosphate, dimyristyl phosphate, dicetyl phosphate and the like. In this embodiment, preferred amount of the phosphoric acid dialkyl ester is from 1 to 50 mass %, more preferably from 1 to 30 mass %, still more preferably from 1 to 20 mass %, based on the total mass of phosphatidylcholine and phosphatidylserine.

In the liposome containing a phosphatidylcholine, a phosphatidylserine, a phosphoric acid dialkyl ester and the compound of the present invention as membrane components, preferred mass ratios of PC, PS, phosphoric acid dialkyl ester and the compound of the present invention is from 5 to 40 mass %: from 5 to 40 mass %: from 1 to 10 mass %: from 15 to 80 mass %.

The components of the liposome of the present invention are not limited to the aforementioned four kinds of compounds, and other components may be admixed. Examples of such components include cholesterol, cholesterol esters, sphingomyelin, monosial ganglioside GM1 derivatives described in FEBS Lett., 223, 42 (1987); Proc. Natl. Acad. Sci., USA, 85, 6949 (1988) and the like, glucuronic acid derivatives described in Chem. Lett., 2145 (1989); Biochim. Biophys. Acta, 1148, 77 (1992) and the like, and polyethylene glycol derivatives described in Biochim. Biophys. Acta, 1029, 91 (1990); FEBS Lett., 268, 235 (1990) and the like However, the components are not limited to these examples.

The liposome of the present invention may be prepared by any methods available for those skilled in this field. Examples of the preparation methods are described in Ann. Rev. Biophys. Bioeng., 9, 467 (1980), "Liopsomes" (Ed. by M. J. Ostro, MARCELL DEKKER, INC.) and the like, as well as the published reviews of liposomes mentioned above. More specifically, examples include the ultrasonication method, ethanol injection method, French press method, ether injection method, cholic acid method, calcium fusion method, freeze and thawing method, reverse phase evaporation method and the like. However, the preparation methods are not limited to these examples. Size of the liposome of the present invention may be any of those obtainable by the aforementioned methods. Generally, the size in average may be 400 nm or less, preferably 200 nm or less. Structure of the liposome is not also particularly limited, and may be any structure such as unilamellar or multilamellar structure. It is also possible to formulate one or more kinds of appropriate medicaments or other contrast media in the liposome.

When the liposomes of the present invention are used as a contrast medium, it can be preferably administered parenterally, more preferably intravenously administered. For example, preparations in the form of an injection or a drip infusion can be provided as powdery compositions in a lyophilized form, and they can be used by being dissolved or resuspended just before use in water or an appropriate solvent (e.g., physiological saline, glucose infusion, buffering solution and the like). When the liposomes of the present invention are used as a contrast medium, the dose can be suitably determined so that the content of compounds in the liposomes becomes similar to that of a conventional contrast medium.

Although it is not intended to be bound by any specific theory, it is known that, in vascular diseases such as arteriosclerosis or restenosis after percutaneous transluminal coronary angioplasty (PTCA), vascular smooth muscle cells constituting tunica media of blood vessel abnormally proliferate and migrate into endosporium at the same time to narrow blood flow passages. Although triggers that initiate the abnormal proliferation of normal vascular smooth muscle cells have not yet been clearly elucidated, it is known that migration into endosporium and foaming of macrophages are important factors. It is reported that vascular smooth muscle cells then cause phenotype conversion (from constricted to composite type).

If the liposomes of the present invention are used, the compound serving as a defined contrast medium can be selectively taken up into the vascular smooth muscle cells abnormally proliferating under influences of foam macrophages. As a result, imaging becomes possible with high contrast between vascular smooth muscle cells of a lesion and a non-pathological site. Therefore, the contrast medium of the present invention can be suitably used particularly for MRI of vascular diseases. For example, imaging of arteriosclerotic lesion or restenosis after PTCA can be performed.

Further, as described in J. Biol. Chem., 265, 5226 (1990), for example, it is known that liposomes containing phospholipids, in particular, liposomes formed from PC and PS, are likely to accumulate on macrophages with the aid of scavenger receptors. Therefore, by using the liposomes of the present invention, the compound of the present invention can be accumulated in a tissue or a lesion in which macrophages localize. If the liposomes of the present invention are used, a predetermined compound can be accumulated in macrophages in a larger amount compared with the case of using suspension or oil emulsion belonging to known techniques.

Examples of tissues in which localization of macrophages is observed, which can be suitably imaged by the method of the present invention, include blood vessel, liver, air vesicle, lymph node, lymph vessel, and renal epithelium. Further, it is known that macrophages accumulate in lesions in certain classes of diseases. Examples of such diseases include tumor, arteriosclerosis, inflammation, infection and the like. Therefore, lesions of such diseases can be identified by using the liposomes of the present invention. In particular, it is known that foam macrophages, which take up a large amount of denatured LDL with the aid of scavenger receptors, accumulate in atherosclerosis lesions at an early stage (Am. J. Pathol., 103, 181 (1981); Annu. Rev. Biochem., 52, 223 (1983)). Therefore, by performing imaging after accumulation of the liposomes of the present invention in the macrophages, it is possible to identify locations of atherosclerosis lesions at an early stage, which is hardly achievable by other means.

The imaging method using the liposomes of the present invention is not particularly limited. For example, imaging can be attained by measuring change in the T1/T2 relaxation time of water in the same manner as that in imaging methods using a usual contrast medium for MRI. Moreover, it is also possible to use the liposomes as a contrast medium for scintigraphy, X-ray contrast medium, optical image formation agent, and ultrasonic contrast agent by suitably using an appropriate metal ion.

EXAMPLES

The present invention will be explained more specifically with reference to the following examples. However, the scope of the present invention is not limited to the following examples.

Example 1

Compound 204, of which structure was shown above, was synthesized from monobenzalpentaerythritol (Compound A) known from literature [described in Org. Syntheses Coll., Vol. 4, 679 (1963)] as a starting material according to the following scheme. Two hydroxy groups of Compound A were condensed with phytanic acid by using a condensing agent, EDC (1-ethyl-3-(3-dimethylamino)propylcarbodiimide hydrochloride), to obtain a diester compound, Compound B [Jikken Kagaku Koza (Lecture of Experimental Chemistry), 4th edition, edited by the Chemical Society of Japan, Maruzen, Vol. 22, p. 258]. The benzylidene group of Compound B was successively removed by catalytic reduction [Hanessian et al, Synthesis, 396 (1981)], and then one of the hydroxy groups was made into an oleic acid ester (Compound C). The other hydroxy group and 8-hydroxyoctanoic acid were condensed to convert the compound into an ω-hydroxy ester compound, Compound $D_{204}$.

The synthesis thereafter was performed according to the method described in Japanese PatentApplication No. 2005-283461. Compound D and Chelate ligand moiety E, which was separately synthesized, were bonded to obtain Compound $F_{204}$. Deprotection of the t-butyl ester was performed under an acidic condition to synthesize Compound 204, and by allowing gadolinium chloride to act on Compound 204, Complex 204-Gd was successfully obtained.

Mass (MALDI-TOF): m/z (α-cyano-4-hydroxycinnamic acid) 1740 (M-Na)⁻

In the following scheme, Ph represents phenyl group, t-Bu represents tertiary butyl group, and Me represents methyl group.

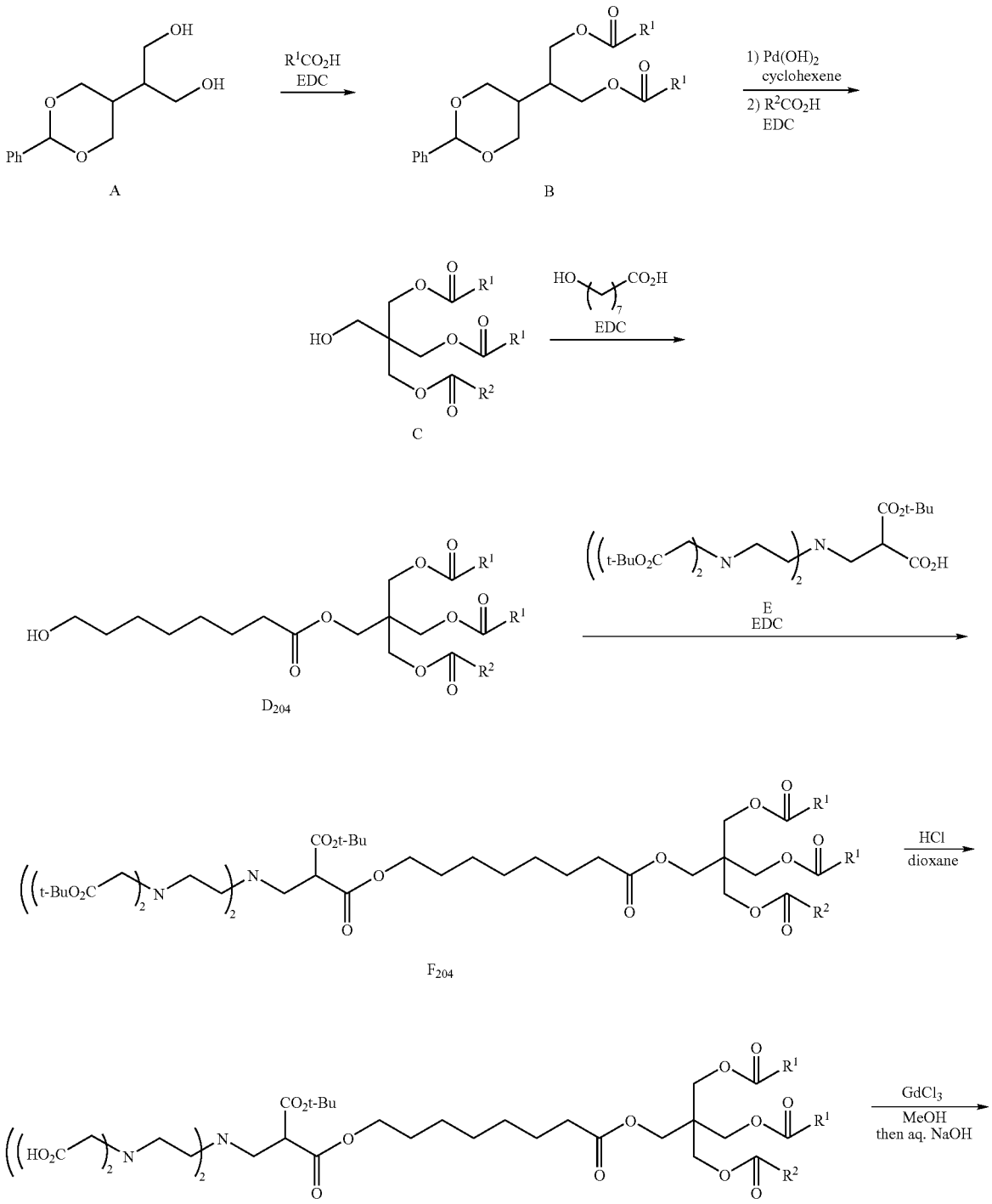

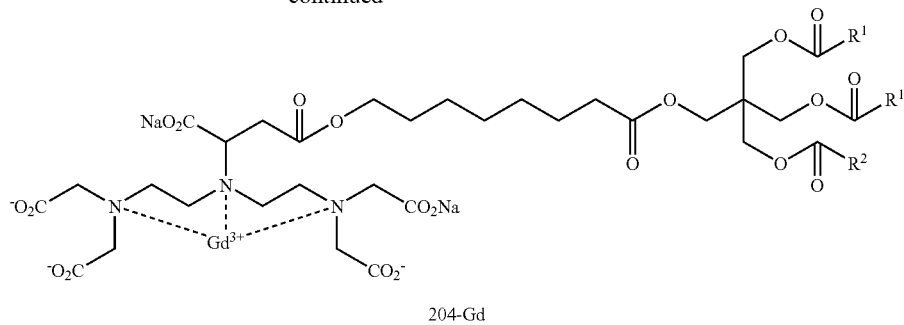

204-Gd

R¹ = CH₂(CH(CH₃)(CH₂)₃)₃CH(CH₃)₂
R² = (CH₂)₇CH═CH(CH₂)₇CH₃

Compound 206, in which L is bonded via an ether bond, was synthesized according to the following scheme. A bromide was allowed to act on Compound C in the presence of a Lewis acid according to the method of Schmidt et al. [Euro. J. Org. Chem., 19, 3979 (2004)] to synthesize Compound G₂₀₆. The hydroxy group of Compound G₂₀₆ and the carboxy group of Compound E were condensed to obtain Compound H. Deprotection of the t-Bu ester was performed under an acidic condition to synthesize Compound 206, and by allowing gadolinium chloride to act on Compound 206, Complex 206-Gd was successfully obtained.

Mass (MALDI-TOF): m/z (α-cyano-4-hydroxycinnamic acid) 1774 (M-Na)⁻

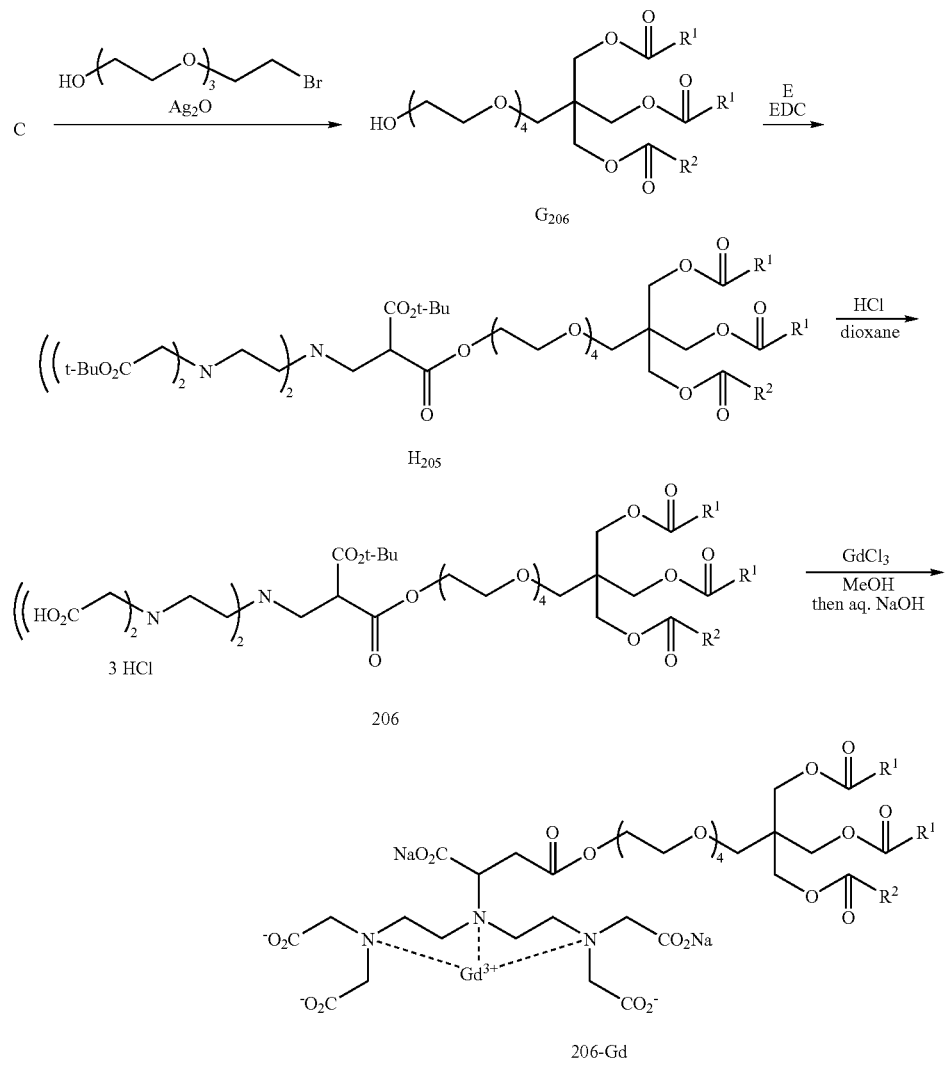

206-Gd

R¹ = CH₂(CH(CH₃)(CH₂)₃)₃CH(CH₃)₂
R² = (CH₂)₇CH═CH(CH₂)₇CH₃

Compound 304, in which $R^1$, $R^2$, and $R^3$ consist of the same substituents, and L and $X^3$ are bonded as carboxylic acid ester, was synthesized by following the route described below. Palmitoyl chloride was allowed to act on commercially available bis(hydroxymethyl)-3-bromo-1-propanol to obtain Triester I. Triester I was reacted with 12-hydroxydodecanoic acid cesium salt according to a known method [literature: J. Org. Chem., 1981, 46, 4321-4323], and thereby converted into Tetraester $J_{304}$.

The synthesis thereafter was performed according to the method described in Japanese Patent Application No. 2005-283461. Compound $J_{304}$ and Chelate ligand moiety C, which was separately synthesized, were bonded to obtain Compound $F_{304}$. Deprotection of the t-butyl ester was performed under an acidic condition to synthesize Compound 304, and by allowing gadolinium chloride to act on Compound 304, Complex 304-Gd was successfully obtained.

Mass (MALDI-TOF): m/z (α-cyano-4-hydroxycinnamic acid) 1658 (M-Na)⁻

In the following scheme, Ph represents phenyl group, t-Bu represents tertiary butyl group, and Me represents methyl group.

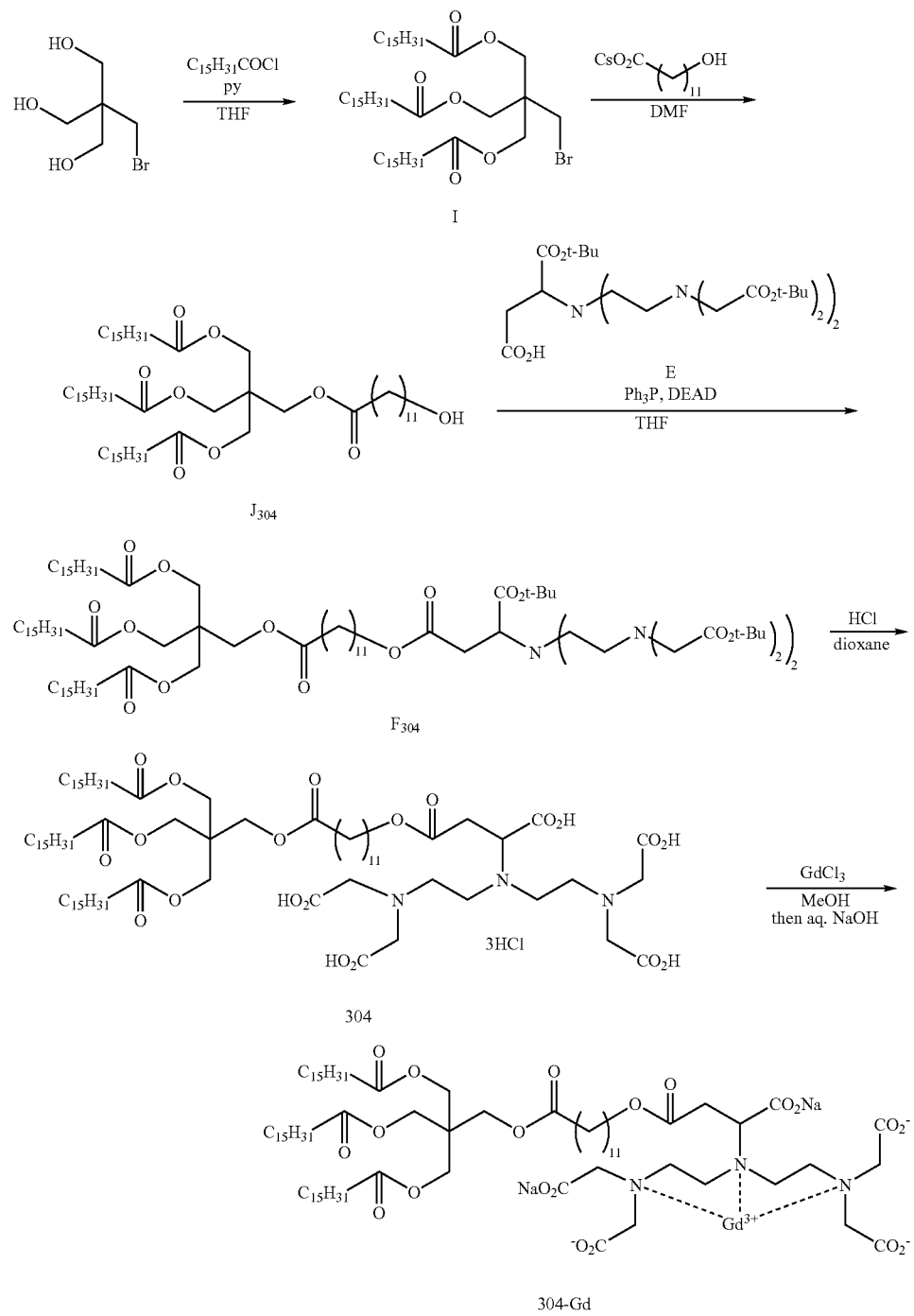

Synthesis Example 4

Compound 407, in which $R^1$, $R^2$, and $R^3$ consist of the same substituents, and L and $X^3$ are bonded as carbonic acid ester, was synthesized by following the route described below. 1,1'-Carbonyldiimidazole and a diol were allowed to act on Compound K, which was obtained by a method known from literature [Euro. J. Org. Chem., 19, 3979 (2004)] to obtain Carbonic acid ester $L_{407}$. Thereafter, Mitsunobu reaction, deprotection under an acidic condition, and complex formation were performed in the same manners as those used for the aforementioned compounds to convert the ester into Complex 407-Gd.

Mass (MALDI-TOF): m/z (α-cyano-4-hydroxycinnamic acid) 1636 (M-Na)⁻

In the following scheme, Ph represents phenyl group, t-Bu represents tertiary butyl group, and Me represents methyl group.

Test Example 1

Solubility Test

Each of the gadolinium complexes shown below was weighed in an amount giving a concentration of 1 mM, and added with 1 ml of chloroform or a mixed solvent of chloroform/methanol (1/1), and solubility in the solvent was examined (at room temperature of 25° C.). As a result, the compounds of the present invention formed uniform solutions unlike Comparative Compound, and thus it is clearly understood that they have superior features for preparation of liposomes.

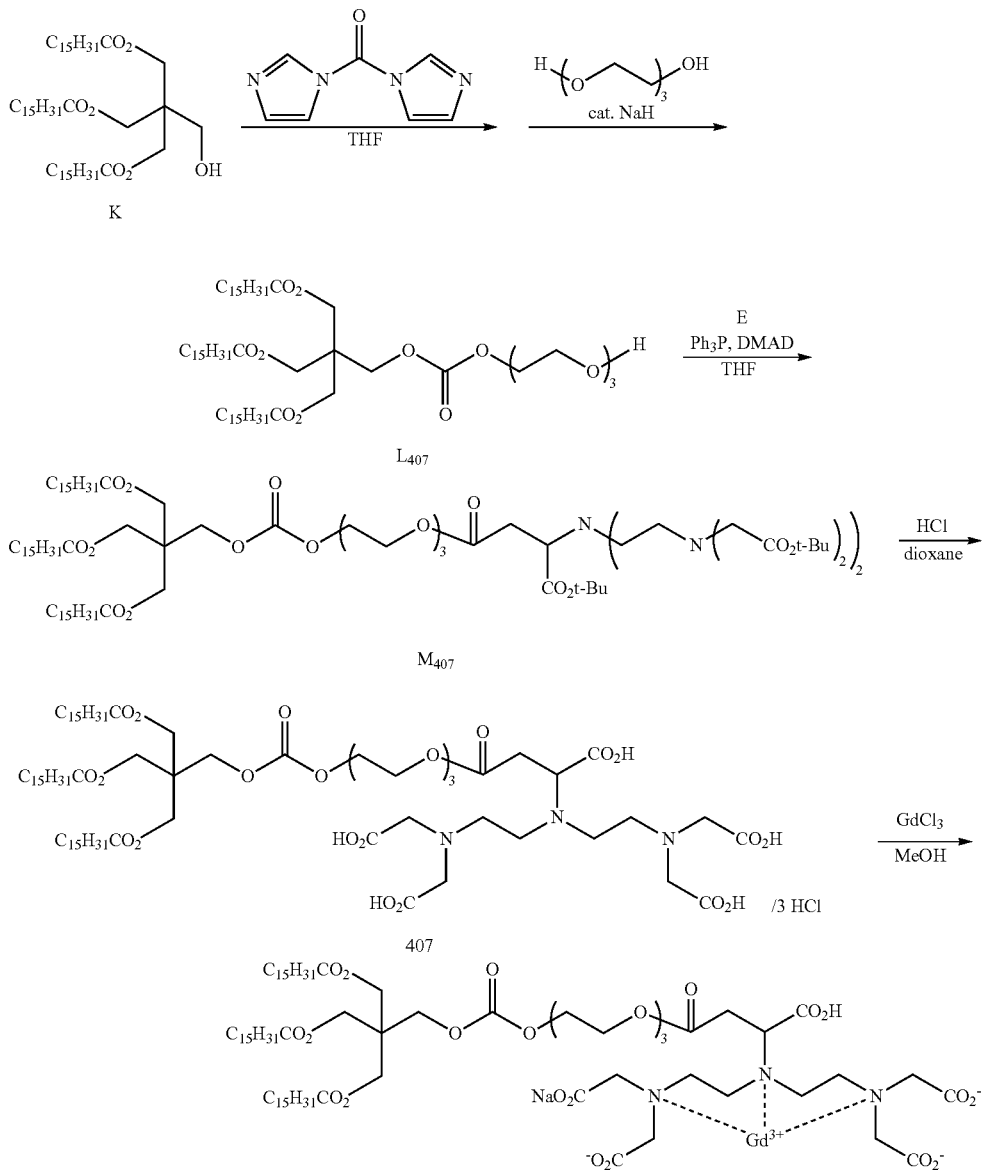

TABLE 4

|  | Chloroform | Chloroform/methanol (1/1) |
|---|---|---|
| Compound 19-Gd: | ○ | ○ |
| Compound 23-Gd: | ○ | ○ |
| Compound 24-Gd: | ○ | ○ |
| Compound 32-Gd: | ○ | ○ |
| Compound 103-Gd: | ○ | ○ |
| Compound 118-Gd: | ○ | ○ |
| Compound 204-Gd: | ○ | ○ |
| Compound 206-Gd: | ○ | ○ |
| Compound 209-Gd: | ○ | ○ |
| Compound 302-Gd: | ○ | ○ |
| Compound 303-Gd: | ○ | ○ |
| Compound 304-Gd: | ○ | ○ |
| Compound 305-Gd: | ○ | ○ |
| Compound 401-Gd: | ○ | ○ |
| Compound 402-Gd: | ○ | ○ |
| Compound 403-Gd: | ○ | ○ |
| Compound 406-Gd: | ○ | ○ |
| Compound 407-Gd: | ○ | ○ |
| Compound 408-Gd: | ○ | ○ |
| Compound 409-Gd: | ○ | ○ |
| Compound 410-Gd: | ○ | ○ |
| Comparative Compound: | X | X |

○: Uniform solution was formed,
X: Other result

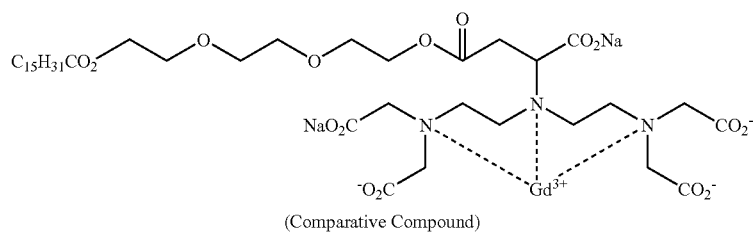

(Comparative Compound)

Test Example 2

Preparation of Liposomes

According to the method described in J. Med. Chem., 25 (12), 1500 (1982), dipalmitoyl-PC (Funakoshi, No. 1201-41-0225), dipalmitoyl-PS (Funakoshi, No. 1201-42-0237), and each of the gadolinium complexes were dissolved in the concentration ratio mentioned below in chloroform contained in an eggplant-shaped flask to form a uniform solution, and then the solvent was evaporated under reduced pressure to form a thin membrane on the bottom of the flask. The thin membrane was dried in vacuo, then added with an appropriate volume of 0.9% physiological saline (Hikari Pharmaceutical, No. 512) and ultrasonicated (probe type oscillator, Branson, No. 3542, 0.1 mW) for 5 minute with ice cooling, and then a liposome preparation apparatus (Central Kagaku) was used to obtain a uniform liposome dispersion in which particles had sizes of 85 to 120 nm.

TABLE 5

| |
|---|
| Concentration ratio: PS 50 nmol + PC 50 nmol + Compound 19-Gd 5 nmol |
| Concentration ratio: PS 50 nmol + PC 50 nmol + Compound 23-Gd 1 nmol |
| Concentration ratio: PS 50 nmol + PC 50 nmol + Compound 24-Gd 5 nmol |
| Concentration ratio: PS 50 nmol + PC 50 nmol + Compound 32-Gd 10 nmol |
| Concentration ratio: PS 50 nmol + PC 50 nmol + Compound 103-Gd 1 nmol |
| Concentration ratio: PS 50 nmol + PC 50 nmol + Compound 118-Gd 1 nmol |
| Concentration ratio: PS 50 nmol + PC 50 nmol + Compound 204-Gd 5 nmol |
| Concentration ratio: PS 50 nmol + PC 50 nmol + Compound 206-Gd 1 nmol |
| Concentration ratio: PS 50 nmol + PC 50 nmol + Compound 209-Gd 10 nmol |
| Concentration ratio: PS 50 nmol + PC 50 nmol + Compound 302-Gd 10 nmol |
| Concentration ratio: PS 50 nmol + PC 50 nmol + Compound 303-Gd 10 nmol |
| Concentration ratio: PS 50 nmol + PC 50 nmol + Compound 304-Gd 5 nmol |
| Concentration ratio: PS 50 nmol + PC 50 nmol + Compound 305-Gd 5 nmol |
| Concentration ratio: PS 50 nmol + PC 50 nmol + Compound 401-Gd 10 nmol |
| Concentration ratio: PS 50 nmol + PC 50 nmol + Compound 402-Gd 20 nmol |
| Concentration ratio: PS 50 nmol + PC 50 nmol + Compound 403-Gd 5 nmol |
| Concentration ratio: PS 50 nmol + PC 50 nmol + Compound 406-Gd 5 nmol |
| Concentration ratio: PS 50 nmol + PC 50 nmol + Compound 407-Gd 1 nmol |
| Concentration ratio: PS 50 nmol + PC 50 nmol + Compound 408-Gd 10 nmol |
| Concentration ratio: PS 50 nmol + PC 50 nmol + Compound 409-Gd 10 nmol |
| Concentration ratio: PS 50 nmol + PC 50 nmol + Compound 410-Gd 10 nmol |

Test Example 3

Toxicity Test by Continuous Administration for 3 Days in Mice

Six-week old ICR male mice (Charles River Japan) were purchased, and after quarantine for 1 week, acclimatized for 1 week in a clean animal cage (air-conditioning: HEPA filter of class 1000, room temperature: 20 to 24° C., humidity: 35 to 60%). Then, in order to obtain the MTD (maximum tolerated dose) value, a mouse serum suspension of a test compound was given from the caudal vein. The mouse serum suspension of a test compound was given by using physiological saline (Hikari Pharmaceutical) or a glucose solution (Otsuka Pharmaceutical) as a solvent. Then, on the basis of the MTD value obtained, Compound 103-Gd mentioned above was given everyday from the caudal vein for three consecutive days in an amount corresponding to ½ of the MTD value (n=3). The symptoms were observed up to 6 hours after each administration to observe neurotoxicity, and then autopsy was performed to examine major organs. The results are shown below. It was successfully confirmed that the compounds of the present invention had low toxicity and no neurotoxicity. Thus, it is clearly understood that the compounds of the present invention have superior characteristics as a component lipid of liposomes for contrast medium.

TABLE 6

| Compound: MTD (mg/kg): Neurotoxicity |
| --- |
| Compound 19-Gd (50 mg/kg): − |
| Compound 23-Gd (50 mg/kg): − |
| Compound 32-Gd (50 mg/kg): − |
| Compound 204-Gd (50 mg/kg): − |
| Compound 209-Gd (50 mg/kg): − |
| Compound 302-Gd (50 mg/kg): − |
| Compound 303-Gd (50 mg/kg): − |
| Compound 304-Gd (50 mg/kg): − |
| Compound 305-Gd (50 mg/kg): − |
| Compound 402-Gd (50 mg/kg): − |
| Compound 403-Gd (50 mg/kg): − |
| Compound 406-Gd (50 mg/kg): − |
| Compound 407-Gd (50 mg/kg): − |
| Compound 408-Gd (50 mg/kg): − |
| Compound 409-Gd (50 mg/kg): − |
| Compound 410-Gd (50 mg/kg): − |

("−" indicates negative for neurotoxicity, and "+" indicates positive for neurotoxicity)

INDUSTRIAL APPLICABILITY

The compound, chelate compound, and a salt of either of said compounds according to the present invention have superior properties as a component lipid of liposomes for contrast medium, and a lesion of a vessel can be selectively contrasted by performing imaging using liposomes containing the compound.

The invention claimed is:

1. A compound represented by the following general formula (I), or a salt thereof:

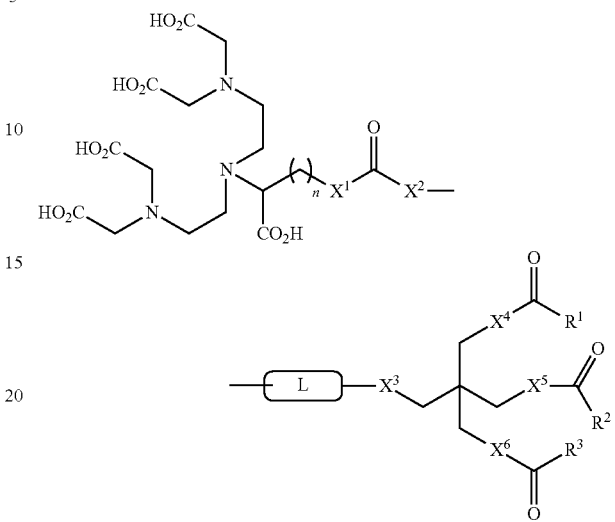

wherein $R^1$, $R^2$ and $R^3$ independently represent an alkyl group having 8 to 30 carbon atoms, which may have a substituent, or an alkenyl group having 8 to 30 carbon atoms, which may have a substituent; $X^1$ and $X^2$ independently represent a single bond, —O—, or —N($Z^1$)- ($Z^1$ represents hydrogen atom, or an alkyl group having 1 to 3 carbon atoms), provided that $X^1$ and $X^2$ do not simultaneously represent a single bond; $X^3$, $X^4$, $X^5$ and $X^6$ independently represent —O—, or —N($Z^2$)- ($Z^2$ represents hydrogen atom, or an alkyl group having 1 to 3 carbon atoms); n represents an integer of 1 to 10; and L represents a divalent bridging group (L is constituted by atoms selected from the group consisting of carbon atom, hydrogen atom, oxygen atom, nitrogen atom, fluorine atom and sulfur atom, wherein the total number of oxygen atom constituting L is 0 to 9, that of nitrogen atom is 0 to 4, that of fluorine atom is 0 to 8, and that of sulfur atom is 0 to 2, and the total number of carbon atom, oxygen atom, nitrogen atom and sulfur atom constituting L is 1 to 20).

2. The compound or a salt thereof according to claim 1, wherein $X^3$ is —O—.

3. The compound or a salt thereof according to claim 1, wherein $X^4$, $X^5$ and $X^6$ represent —O—.

4. The compound or a salt thereof according to claim 1, wherein $X^2$ is —O—, or —N($Z^1$)- ($Z^1$ represents hydrogen atom, or a lower alkyl group having 1 to 3 carbon atoms).

5. The compound or a salt thereof according to claim 1, wherein L is an alkylene group having 1 to 12 carbon atoms, or a bridging group represented by —($CH_2CH_2Y$)$_m$$CH_2CH_2$— (m represents an integer of 1 to 6, Y represents —O—, or —N($Z^3$)- ($Z^3$ represents hydrogen atom, methyl group, or phenyl group), and when m is 2 or larger, two or more of groups Y may be the same or different).

6. The compound or a salt thereof according to claim 1, wherein L is a bridging group represented by —($CH_2CH_2Y$)$_m$$CH_2CH_2$— (m represents an integer of 1 to 6, Y represents —O—, or —N($Z^3$)- ($Z^3$ represents hydrogen atom, methyl group, or phenyl group), and when m is 2 or larger, two or more of groups Y may be the same or different).

7. The compound or a salt thereof according to claim 1, wherein L is a bridging group represented by —($CH_2CH_2O$)$_l$$CH_2CH_2$— (l represents an integer of 1 to 6).

8. The compound or a salt thereof according to claim 1, wherein L is a bridging group represented by -$T^1$-CO-($T^1$ is an alkylene group having 1 to 14 carbon atoms, or a group represented by the general formula —$(CH_2CH_2Y)_u(CH_2)_h$— (u represents an integer of 1 to 6, h represents an integer of 0 to 2, Y represents —O—, or —N($Z^3$)- ($Z^3$ represents hydrogen atom, methyl group, or phenyl group), and when u is 2 or larger, two or more of groups Y may be the same or different).

9. The compound or a salt thereof according to claim 1, wherein L is a bridging group represented by -$T^2$-$X^7$CO— ($X^7$ represents —O—, or N($Z^4$)- ($Z^4$ represents hydrogen atom, or methyl group), and $T^2$ represents an alkylene group having 1 to 14 carbon atoms).

10. The compound or a salt thereof according to claim 1, wherein L contains at least one 3- to 20-membered ring structure in the main chain thereof.

11. The compound or a salt thereof according to claim 1, wherein $R^1$, $R^2$, and $R^3$ independently represent a linear alkyl group having 10 to 22 carbon atoms, a linear alkenyl group having 10 to 22 carbon atoms, a branched alkyl group having 10 to 22 carbon atoms, or a branched alkenyl group having 10 to 22 carbon atoms.

12. A chelate compound or a salt thereof, which consists of the compound or a salt thereof according to claim 1 and a metal ion.

13. The chelate compound or a salt thereof according to claim 12, wherein the metal ion is a metal ion of an element selected from the elements of the atomic numbers 21 to 29, 31, 32, 37 to 39, 42 to 44, 49, and 57 to 83.

14. The chelate compound or a salt thereof according to claim 12, wherein the metal ion is a metal ion of a paramagnetic element selected from the elements of the atomic numbers 21 to 29, 42, 44, and 57 to 71.

15. A liposome containing the compound or a salt thereof according to claim 1 as a membrane component.

16. The liposome according to claim 15, which contains a phosphatidylcholine and a phosphatidylserine as membrane components.

17. A contrast medium, which comprises the liposome according to claim 15.

18. The contrast medium according to claim 17, which is used for imaging of a vascular disease.

19. The contrast medium according to claim 17, which is used for imaging of vascular smooth muscle cells abnormally proliferating under influence of foam macrophages.

20. The contrast medium according to claim 17, which is used for imaging of a tissue or lesion in which macrophages localize.

21. The contrast medium according to claim 20, wherein the tissue in which macrophages localize is selected from the group consisting of tissues of liver, spleen, air vesicle, lymph node, lymph vessel, and renal epithelium.

22. The contrast medium according to claim 20, wherein the lesion in which macrophages localize is selected from the group consisting of lesions of tumor, inflammation, and infection.

* * * * *